United States Patent
Ayame et al.

(10) Patent No.: US 6,635,012 B2
(45) Date of Patent: Oct. 21, 2003

(54) ELECTRONIC ENDOSCOPE APPARATUS PROVIDED WITH AC LIGHTING LIGHT SOURCE (75) Inventors: Daisuke Ayame, Saitama (JP); Shinji Takeuchi, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 10/109,050

(22) Filed: Mar. 29, 2002

(65) Prior Publication Data
US 2002/0163575 A1 Nov. 7, 2002

(30) Foreign Application Priority Data
Mar. 30, 2001 (JP) .......................................... 2001-102276

(51) Int. Cl.[7] .............................. A61B 1/06; F21V 8/00
(52) U.S. Cl. ......................... 600/178; 362/574; 362/551
(58) Field of Search ................................. 600/178, 182, 600/160; 348/68; 385/147, 901; 362/572, 574, 554, 296, 551; 313/113

(56) References Cited
U.S. PATENT DOCUMENTS

| 4,483,585 A | * | 11/1984 | Takami ........................ 385/115 |
| 4,747,660 A | * | 5/1988 | Nishioka et al. ............... 385/31 |
| 5,331,950 A | * | 7/1994 | Wood, Sr. ...................... 600/109 |
| 5,838,860 A | * | 11/1998 | Kingstone et al. ........... 385/100 |
| 5,971,576 A | * | 10/1999 | Tomioka et al. .............. 362/574 |
| 6,274,970 B1 | * | 8/2001 | Capobianco ................. 313/113 |
| 6,304,693 B1 | * | 10/2001 | Buelow, II et al. ........... 385/31 |
| 6,356,700 B1 | * | 3/2002 | Strobl ........................... 385/147 |
| 2002/0012252 A1 | * | 1/2002 | Carter et al. ................. 362/558 |

* cited by examiner

Primary Examiner—John P. Leubecker
(74) Attorney, Agent, or Firm—Snider & Associates; Ronald R. Snider (57) ABSTRACT

In an apparatus using an AC lighting lamp including a reflector and a condensing lens as a condensing unit and using a CCD to pick up an image of a subject irradiated with a light from the lamp, an entrance facet of a light guide is arranged between two condensing points $G_1$ and $G_2$ and at a position that is not close to either of the condensing points, particularly at an intermediate position therebetween so that lights from a bright spot $g_1$ or $g_2$ at a tip of a first or second electrode, respectively, of the lamp are condensed at the corresponding condensing point by the condensing unit. Thereby, although an amount of emission slightly decreases compared to the case where the entrance facet is arranged on the basis of the bright spot, emission with a reduced variation in luminance is obtained to enable photographing with a substantially uniform amount of exposure, while preventing possible flickers.

3 Claims, 8 Drawing Sheets

ONLY REFLECTOR PROVIDED AND FIRST BRIGHT SPOT ALIGEND WITH REFLECTOR FOCUS

ONLY REFLECTOR PROVIDED AND SECOND BRIGHT SPOT ALIGEND WITH REFLECTOR FOCUS

FIG.1

ONLY REFLECTOR PROVIDED AND FIRST BRIGHT
SPOT ALIGEND WITH REFLECTOR FOCUS

FIG.2

ONLY REFLECTOR PROVIDED AND SECOND BRIGHT
SPOT ALIGEND WITH REFLECTOR FOCUS

FIG. 3

REFLECTOR AND CONDENSING LENS PROVIDED AND
FIRST BRIGHT SPOT ALIGEND WITH REFLECTOR FOCUS

FIG. 4

REFLECTOR AND CONDENSING LENS PROVIDED AND
SECOND BRIGHT SPOT ALIGEND WITH REFLECTOR FOCUS

FIG. 13(A) ODD FIELD ($f_q > f_c$) PRIOR ART

FIG. 13(B) EVEN FIELD ($f_q > f_c$)

FIG. 13(C) ODD FIELD ($f_q \leq f_c$)

FIG. 13(D) EVEN FIELD ($f_q \leq f_c$)

ELECTRONIC ENDOSCOPE APPARATUS PROVIDED WITH AC LIGHTING LIGHT SOURCE

BACKGROUND OF THE INVENTION

This application claims the priority of Japanese Patent Applications No. 2001-102276 filed on Mar. 30, 2001 which is incorporated herein by reference.

1. Field of the Invention

The present invention relates to the structure of a light source section of an electronic endoscope apparatus that supplies a subject with a light using an AC lighting lamp that discharges and lights when provided with an alternating current.

2. Description of the Related Art

With an electronic endoscope apparatus, a light source light is guided from a light source device or the like to a tip portion of a scope via a light guide. Then, an image pickup device such as a CCD (Charge Coupled Device) is used to pickup an image of a subject on the basis of light irradiation from the tip portion so that the subject is displayed on a monitor. In recent years, it has been proposed that an AC lighting lamp, also called a "high-luminance discharge lamp" or the like, be used as a light source for the light source device.

That is, compared to halogen lamps, that is, filament lamps that light when tungsten wires contained therein are heated, or other similar lamps, xenon lamps and metal halide lamps, both of which are discharge lamps, are advantageous in that they efficiently emit a light and withstand long use. Further, endoscopes have a thin light guide corresponding to a scope having a reduced diameter, so that discharge lamps having a smaller luminous bright spot allow a light to impinge more efficiently on the thin light guide.

Figure 11:
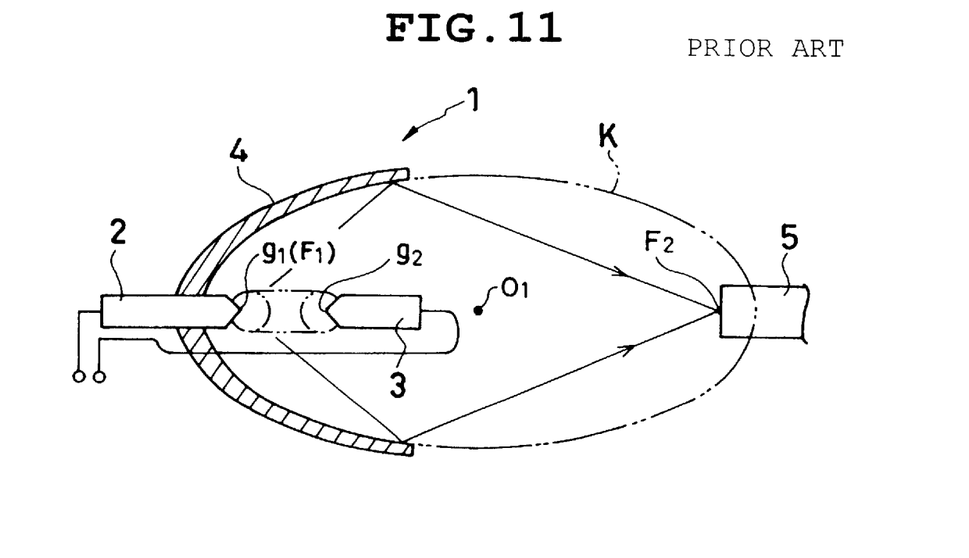
FIG. 11 is a view showing a configuration of a light source section using a conventional AC lighting lamp.

FIG. 11 shows a configuration of an AC lighting lamp (discharge lamp). A lamp 1 in FIG. 11 is composed of a first electrode (cathode) 2 having a sharply angled tip, a second electrode (anode) 3 having a similarly shaped tip, and a reflector 4. If the reflector 4 has a reflecting surface shaped like, for example, an ellipse K (which has a center $O_1$), a bright spot $g_1$ of the sharply-angled tip of the first electrode 2 is arranged at a first focus $F_1$ of the ellipse K, with an entrance facet of a light guide 5 arranged at a second focus $F_2$. With this AC lighting lamp 1, lights emitted from the bright spot $g_1$ are condensed at the second focus $F_2$ by the reflector 4, and the condensed light is guided to the tip portion of the scope via the light guide 5.

However, with an electronic endoscope apparatus using the AC lighting lamp 1, a current applied between the electrodes alternately changes its direction (positive or negative), and the two bright spots $g_1$ and $g_2$ are alternately lighted. If the lighting frequency is lower than the frequency (cycle) at which an image pickup device such as a CCD accumulates charges, an exposure difference may occur between fields to cause flickers.

Figure 12A:
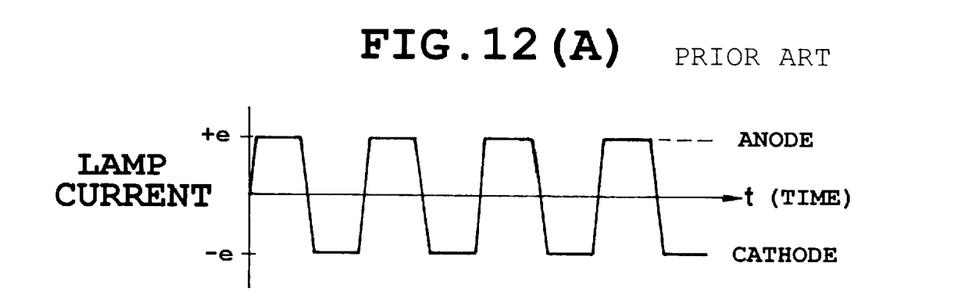
FIG. 12(A) is a waveform diagram showing an alternating current applied to the AC lighting lamp in FIG. 11.
Figure 12B:
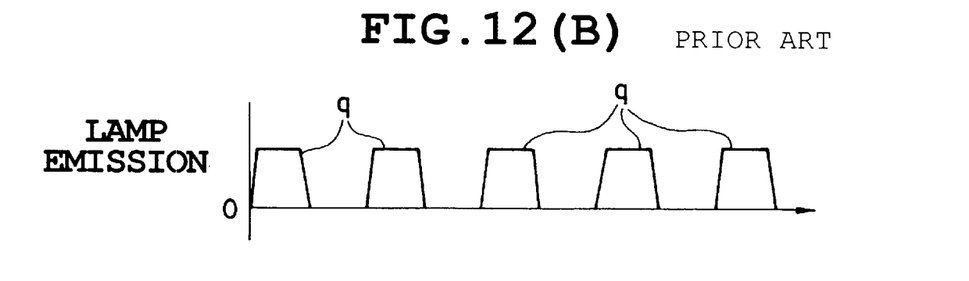
FIG. 12(B) is a waveform diagram showing an emission state of the AC lighting lamp in FIG. 11.

FIGS. 12(A) and 12(B) show an AC current applied to the AC lighting lamp 1 and a lamp emission state. As shown in FIG. 12(A), the lamp 1 alternates between application of a −e voltage to the first electrode (cathode) 2 and application of a +e voltage to the second electrode (anode) 3. As shown in FIG. 12(B), lighting q (lighting frequency $f_q$) is intermittently carried out at the bright spot $g_1$ in FIG. 11.

Figure 13A:
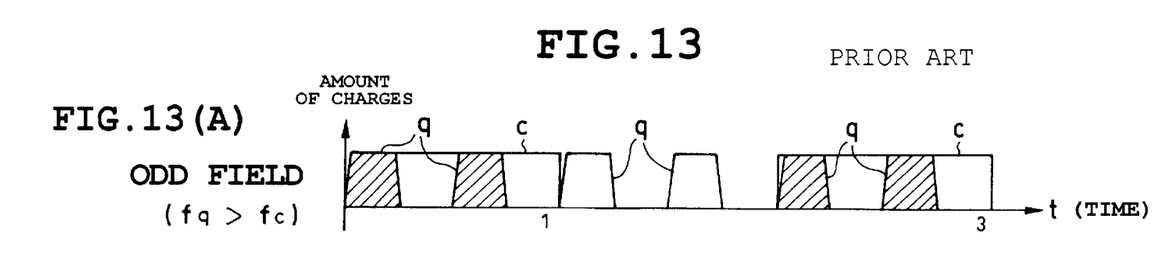
FIGS. 13(A) to 13(D) are timing charts for a conventional endoscope apparatus, showing a relationship between an amount of charges accumulated in a CCD and lighting of a lamp.
Figure 13B:
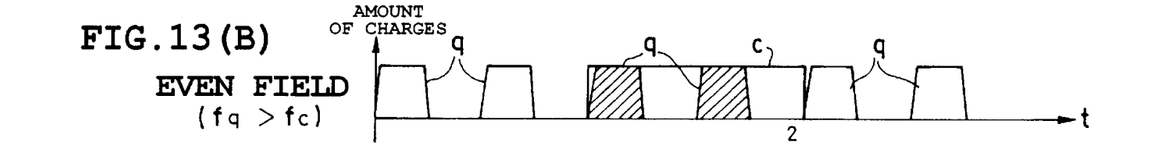
Figure 13C:
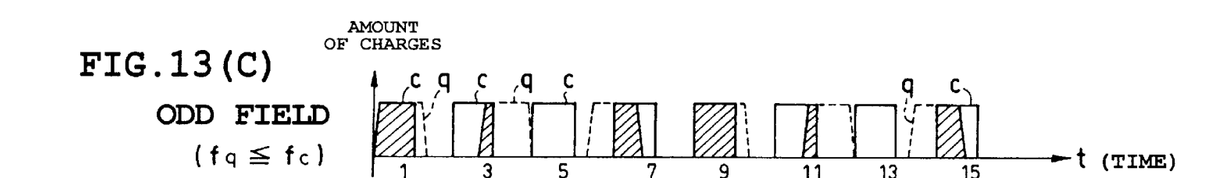
Figure 13D:
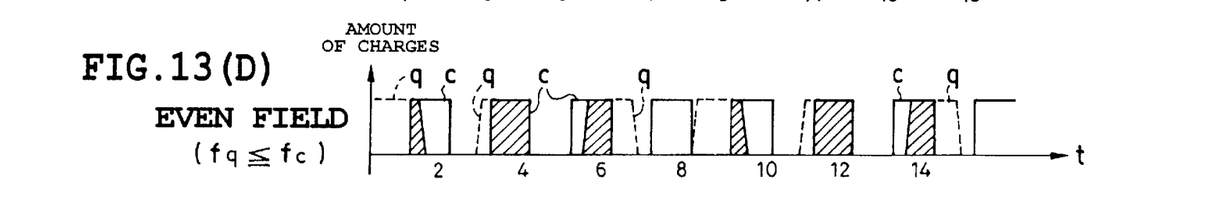

FIGS. 13(A) to 13(D) show the relationship between the accumulation of charges in the CCD and the lighting of the lamp. If the frequency $f_q$ of the lighting q of the lamp 1 is higher than the frequency (vertical synchronizing signal frequency) $f_c$ of charge accumulation c ($f_q > f_c$), two lightings q (shaded portions) are uniformly carried out within the time of charge accumulation c as shown by the odd and even fields in FIGS. 13(A) and 13(B). However, If the frequency $f_q$ is lower than the frequency $f_c$ of charge accumulation c ($f_q \leq f_c$), then as shown by the odd and even fields in FIGS. 13(C) and 13(D), the lightings (emissions) q are not uniformly carried out within the time of charge accumulation c as shown by shaded portions. As a result, the amount of exposure varies between the fields, and when the odd fields in FIG. 13(C) and the even fields in FIG. 13(D) are superimposed on each other so that the former alternates with the latter, flickers may occur on the screen.

SUMMARY OF THE INVENTION

The present invention is achieved in view of the above problems, and it is an object thereof to provide an electronic endoscope apparatus provided with an AC lighting light source that allows images to be picked up with a uniform amount of emission even if the lighting frequency is lower than the frequency of charge accumulation within the corresponding time, thereby preventing the occurrence of flickers.

To attain the above object, the present invention is characterized by comprising an AC lighting light source having condensing means, a light guide that guides a light from the light source to a tip portion of a scope, and an image pickup element that picks up an image of a subject irradiated with a light via the light guide, wherein an entrance facet of the light guide is arranged between two condensing points and at a position that is not close to either of the condensing points so that lights from a bright spot at the tip of each of two electrodes of the AC lighting light source are condensed at the corresponding condensing point by the condensing means.

If as the condensing means for the AC lighting light source, a reflector is arranged opposite the light guide relative to the light source, when an arc gap length between the two electrodes is defined as $\Delta l$, then the entrance facet of the light guide may be arranged close to a position located at a distance $+(\Delta l/2)$ or $-(\Delta l/2)$ from the condensing point formed on the basis of the shape of the reflector.

If as the condensing means for the AC lighting light source, a reflector is arranged opposite the light guide relative to the light source and a condensing lens is arranged on the same side as that of the light guide relative to the light source, when the arc gap length between the two electrodes is defined as $\Delta l$, the focal distance of the condensing lens is defined as f, and the distance from the front focal position of the condensing lens to the focal position of the reflector is defined as x, then the entrance facet of the light guide is preferably arranged close to a position located at the distance indicated by Equation 1, shown below, from the condensing point formed by the reflector and condensing lens.

$$+\frac{f^2 \cdot \Delta l}{2x(x+\Delta l)} \text{ or } -\frac{f^2 \cdot \Delta l}{2x(x+\Delta l)} \qquad \text{[Equation 1]}$$

In the AC lighting light source, a large amount of emission from the two luminous bright spots present at the tips of the respective electrodes is not obtained between these bright spots. However, discharge emission reciprocating between the two electrodes yields emission with a reduced temporal variation in luminance. The present invention utilizes such emission with a reduced temporal variation in luminance, and the entrance facet of the light guide is arranged between the two condensing points so that lights from one of the two bright spots are condensed at the corresponding condensing point by the reflector or condensing lens.

Preferably, if only the reflector is provided, the entrance facet of the light guide is arranged close to the position located at the distance $\pm(\Delta l/2)$ from the corresponding condensing point. If both reflector and condensing lens are provided, the entrance facet is arranged close to the position located at the distance $\pm\{f^2 \cdot \Delta l/[2x(x+\Delta l)]\}$ from the corresponding condensing point. This provides the light guide with a light having a reduced temporal variation in luminance, and affords a substantially uniform amount of emission (amount of exposure) even if the lighting frequency is lower than the frequency of charge accumulation.

DETAILED DESCRIPTION OF THE PREFERRED EMBODIMENTS

Figure 3:
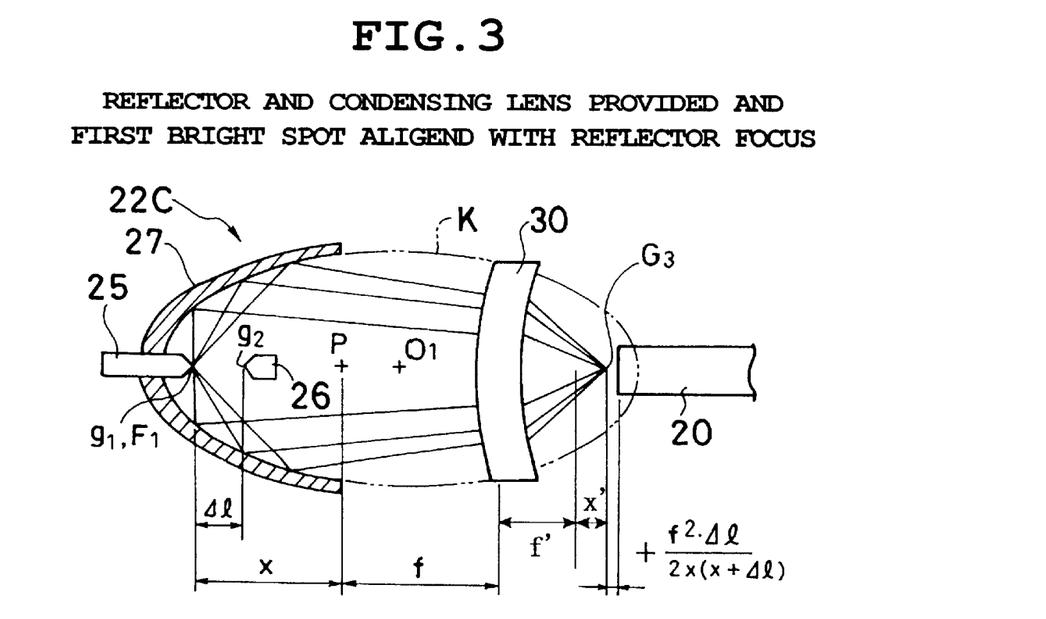
FIG. 3 is a view showing a configuration in which the light source section has a reflector and a condensing lens according to a third embodiment.
Figure 4:
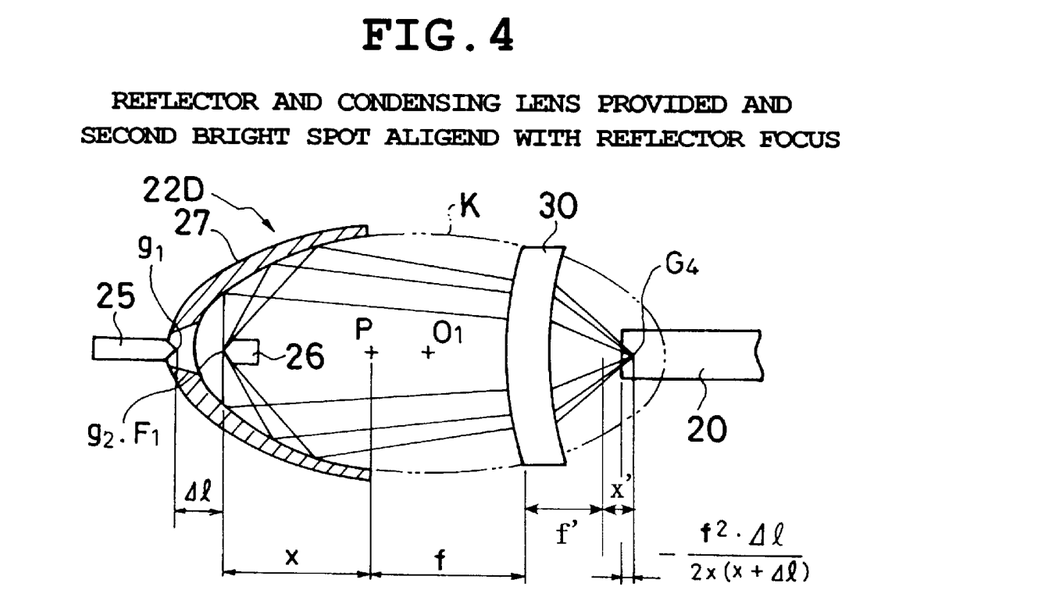
FIG. 4 is a view showing a configuration in which the light source section has a reflector and a condensing lens according to a fourth embodiment.
Figure 5:
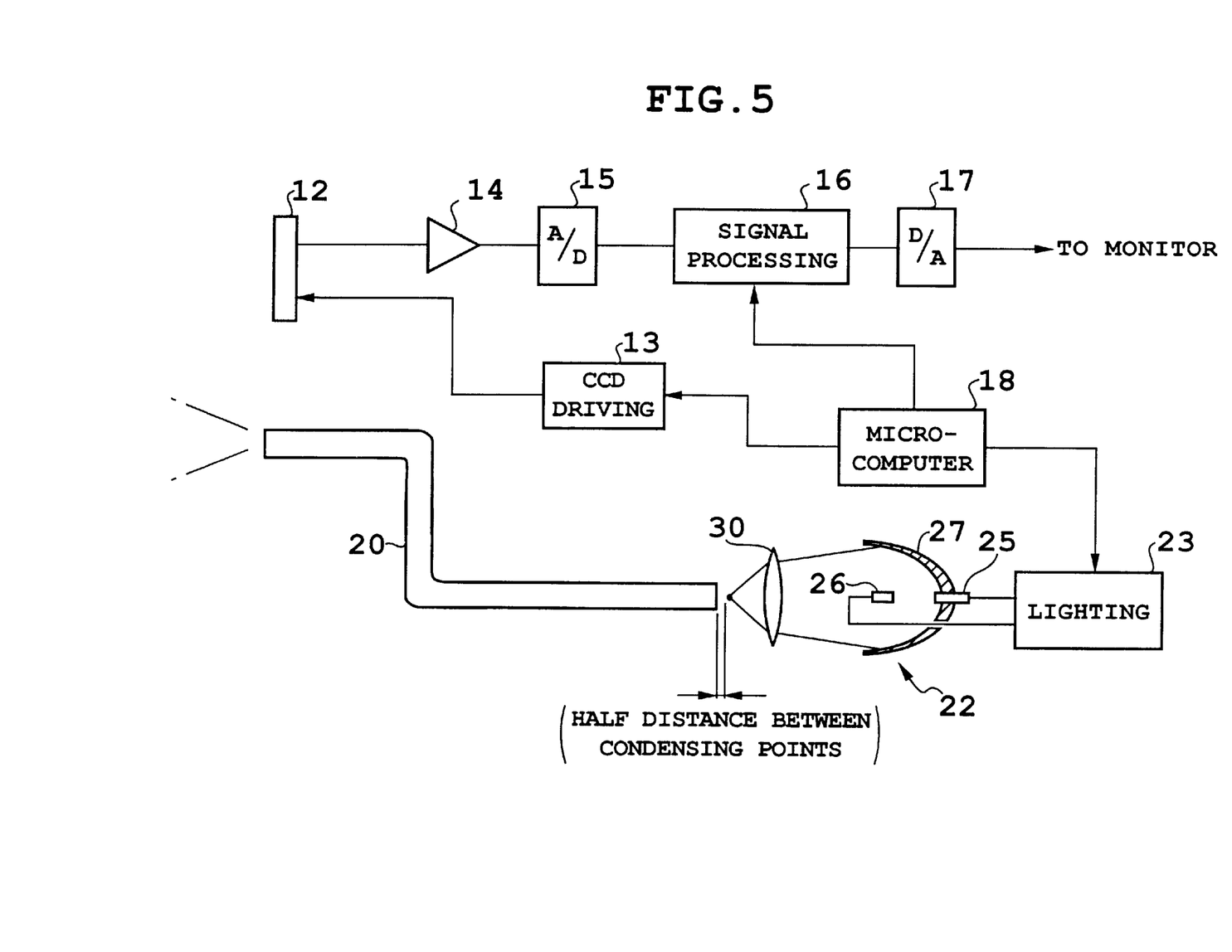
FIG. 5 is a block diagram showing an entire configuration of the electronic endoscope apparatus according to the embodiments.

FIGS. 1 to 4 show configurations of a light source section of an electronic endoscope apparatus according to a first to fourth embodiments, and FIG. 5 shows a configuration of an entire apparatus. First, the entire apparatus will be described. In FIG. 5, a CCD 12 as an image pickup element is provided at a tip portion of a scope and has a CCD driving circuit 13 connected thereto so that the CCD driving circuit 13 allows charges accumulated in the CCD 12 for a predetermined time as pixels to be read out as video data. Further, the CCD driving circuit 13 provides an electronic shutter function of variably controlling the charge accumulation time as a shutter speed.

On the other hand, toward an output of the light source section, the CCD 12 is followed by a signal processing circuit 16 via an amplifier 14, an A/D converter 15, and others. The signal processing circuit 16 executes various processes such as white balancing and gamma correction. The signal processing circuit 16 forms a video signal composed of, for example, a Y (luminance) signal and a C (color) signal or an RGB signal. Then, the output video signal from the signal processing circuit 16 is supplied to a monitor via a D/A converter 17 so that an animated or still image of a subject is displayed on the monitor. Further, a microcomputer 18 is provided to control the above circuits and the light source section.

Furthermore, a light guide 20 is disposed so as to extend from a tip portion of the scope to a light source device having an AC lighting (discharge) lamp 22, a lighting circuit 23, and other components installed therein. The lighting circuit 23 supplies an alternating current of a predetermined frequency to the AC lighting lamp 22 to cause the lamp 22 to discharge and light. Lamp driving frequency can be arbitrarily set.

Figure 1:
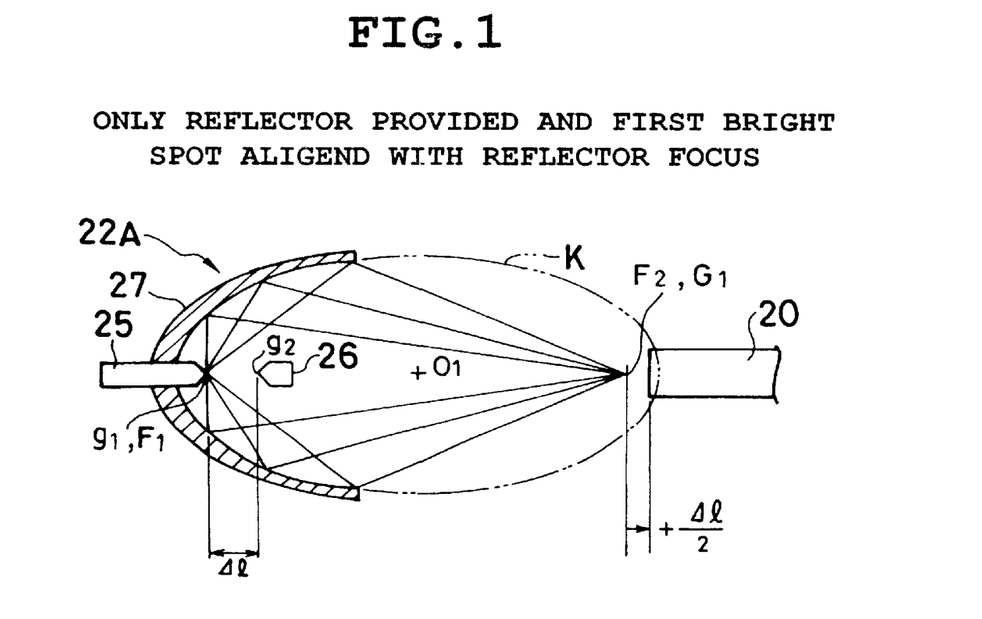
FIG. 1 is a view showing a configuration in which a light source section of an electronic endoscope apparatus has only a reflector according to a first embodiment of the present invention.

FIG. 1 shows a configuration of a first embodiment of a light source section of the light source device. In the first embodiment, only a reflector is provided as condensing means, and a first bright spot is located at the focal position of the reflector. That is, an AC lighting lamp 22A is composed of a first electrode (cathode) 25 having a sharply angled tip, a second electrode (anode) 26 having a similarly shaped tip, and a reflector 27. A first bright spot $g_1$ at a sharply-angled tip of the first electrode 25 is arranged at a first focus $F_1$ of an ellipse K (which has a center $O_1$) of a reflecting surface of the reflector 27. A sharply-angled tip of the second electrode 26, which forms a second bright spot $g_2$, is separated from the first bright spot $g_1$ by an arc gap length (the distance between the tips of the first and second electrodes 25 and 26) $\Delta l$.

In this case, a light generated at the first bright spot $g_1$ is condensed at a second focus $F_2$ of the ellipse K of the reflecting surface of the reflector 27, and the second focus $F_2$ is aligned with a condensing point $G_1$. An entrance facet of the light guide 20 is arranged at a position located at a distance $+(\Delta l/2)$ from the condensing point $G_1$ (the position located in a positive direction relative to a light traveling direction).

Figure 2:
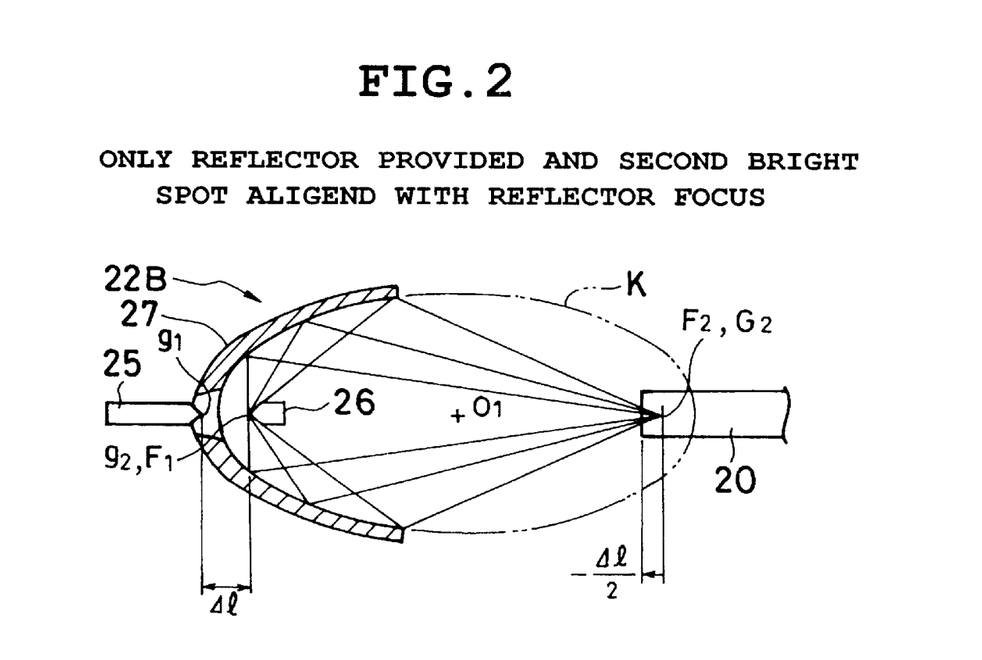
FIG. 2 is a view showing a configuration in which the light source section has only a reflector according to a second embodiment.

FIG. 2 shows a configuration of a second embodiment of the light source section. In the second embodiment, only the reflector is provided as condensing means, and the second bright spot is aligned with the focal position of the reflector. That is, an AC lighting lamp 22B in this case is composed of the first electrode 25, the second electrode 26, and the reflector 27, as in the first embodiment, but the second bright spot $g_2$ at the sharply-angled tip of the second electrode 26 is arranged at the first focus $F_1$ of the ellipse K of the reflecting surface of the reflector 27. Then, in this case, a light generated at the second bright spot $g_2$ is condensed at the second focus $F_2$ Of the ellipse K of the reflecting surface of the reflector 27, and the second focus $F_2$ forms the condensing point $G_2$. Accordingly, the entrance facet of the light guide 20 is arranged at a position located at a distance $-(\Delta l/2)$ from the condensing point $G_2$ (the position in a negative direction relative to the light traveling direction).

FIG. 3 shows a configuration of a third embodiment of the light source section. In the third embodiment, the reflector and the condensing lens are provided as condensing means, and the first bright spot is aligned with the focal position of the reflector. That is, an AC lighting lamp 22C is composed of the first electrode 25 (cathode), the second electrode 26 (anode), and the reflector 27, as in the first embodiment, and the first bright spot $g_1$ at the sharply-angled tip of the first electrode 25 is arranged at the first focus $F_1$ of the ellipse K of the reflecting surface of the reflector 27.

A condensing lens 30 of a focal distance f is arranged in front of the lamp 22C. In the third embodiment, a light generated at the first bright spot $g_1$ is condensed at a condensing point $G_3$ determined by the ellipse K of the reflecting surface of the reflector 27 and the focal distance f of the condensing lens 30. That is, the condensing point $G_3$ is located at a distance $x'=[-f^2/(x+\Delta l)](1+\Delta l/x)$ from the position of a focal distance f' (f'=f) from the condensing lens 30, which position is located closer to the light guide 20 relative to the condensing lens 30. In this case, as shown in the drawing, if the distance from a front focal position P of the condensing lens 30 to the first focus $F_1$ of the reflector 27 is defined as x, the entrance facet of the light guide 20 is arranged close to a position located at a distance $+\{f^2 \cdot \Delta l/[2x(x+\Delta l)]\}$ from the condensing point $G_3$.

FIG. 4 shows a configuration of a fourth embodiment of the light source section. In the fourth embodiment, the reflector and the condensing lens are provided as condensing means, and the second bright spot is aligned with the focal position of the reflector. That is, an AC lighting lamp 22D is composed of the first electrode 25 (cathode), the second electrode 26 (anode), and the reflector 27, and the second bright spot $g_2$ at the sharply-angled tip of the second electrode 26 is arranged at the first focus $F_1$ of the ellipse K of the reflecting surface of the reflector 27.

The condensing lens 30 of the focal distance f is arranged in front of the lamp 22D. In this example, a light generated at the second bright spot $g_2$ is condensed at a condensing point $G_4$ determined by the ellipse K of the reflecting surface of the reflector 27 and the focal distance f of the condensing lens 30. The entrance facet of the light guide 20 is arranged close to a position located at a distance $-\{f^2 \cdot \Delta l/[2x(x+\Delta l)]\}$ from the condensing point $G_4$.

The embodiments are constructed as described above. Now, the operations thereof will be described.

Figure 6:
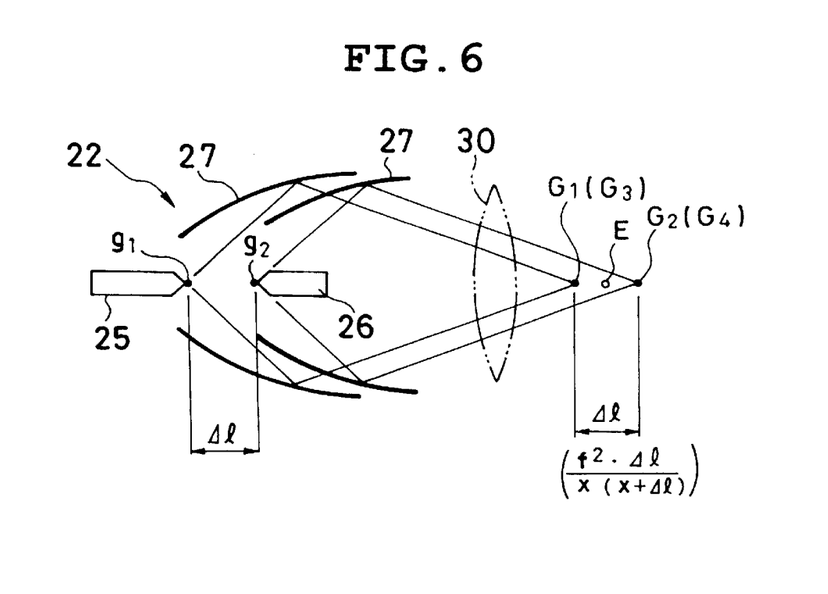
FIG. 6 is a view illustrating all the configurations of the light source section in the embodiments together.

FIG. 6 shows all configurations of the above embodiments together. In the first embodiment, a light is condensed at the point $G_1$, and in the second embodiment, a light is condensed at the point $G_2$. However, in both embodiments, the entrance facet of the light guide 20 is arranged at an intermediate point E between the condensing points $G_1$ and $G_2$. Further, with the condensing lens 30, in the third embodiment, a light is condensed at the point $G_3$, and in the fourth embodiment, a light is condensed at the point $G_4$ (the distance between the points $G_3$ and $G_4$ is different from that between the points $G_1$ and $G_2$). However, in both embodiments, the entrance facet of the light guide 20 is arranged at the intermediate point E between the condensing points $G_3$ and $G_4$. The entrance facet of the light guide 20 may be arranged at a position located between the condensing points $G_1$ and $G_2$ or $G_3$ and $G_4$ but not close to any of the condensing points $G_1$ to $G_4$.

Figure 7:
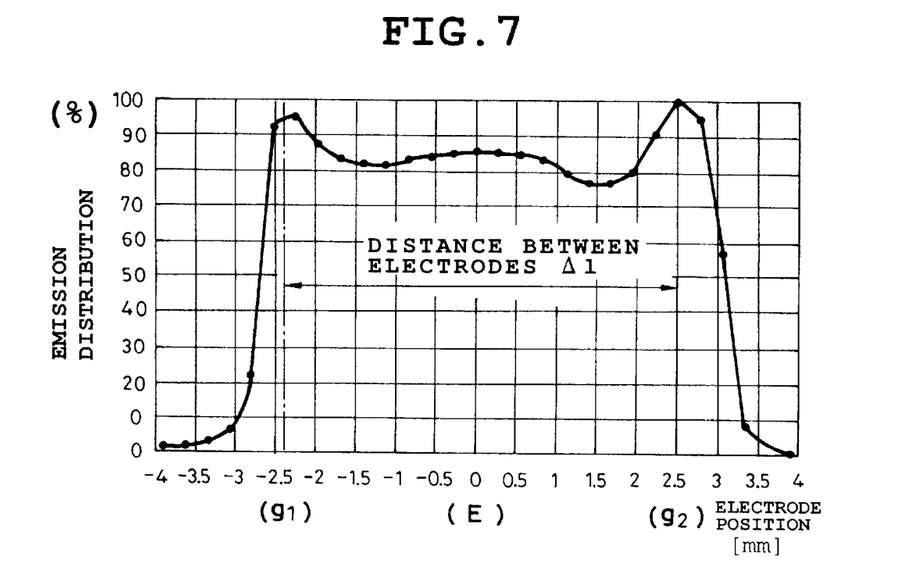
FIG. 7 is a graph showing a distribution of emission from electrodes of an AC lighting lamp in the embodiments.

FIG. 7 shows a distribution of emission from the electrodes of the AC lighting lamp 22. As shown in the drawing, if substantially 100% of the whole emission is provided at the first bright spot $g_1$ of the first electrode 25 and the second bright spot $g_2$ of the second electrode 26, then about 85% of the whole emission, which is sufficient for practical use, is provided even at the intermediate point E between the condensing points $G_1$ and $G_2$ or $G_3$ and $G_4$. Furthermore, emission with a reduced temporal luminance difference is yielded at the intermediate point E.

Figure 8:
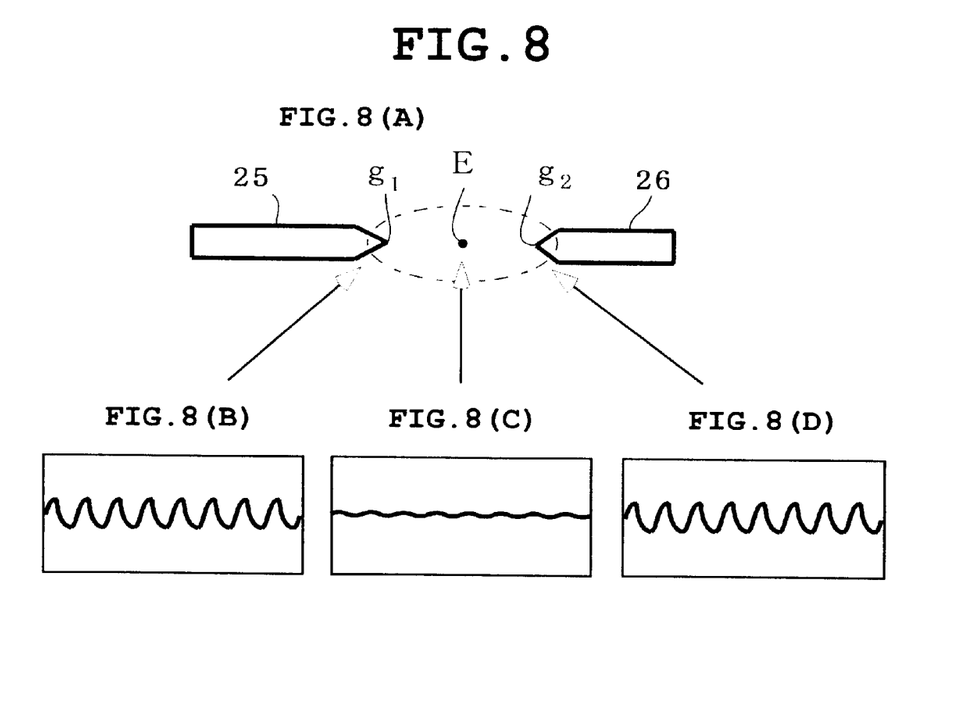
FIGS. 8(A) to 8(D) are diagrams showing variations in a luminance of emission from electrodes of the AC lighting lamp in the embodiments.
Figure 9:
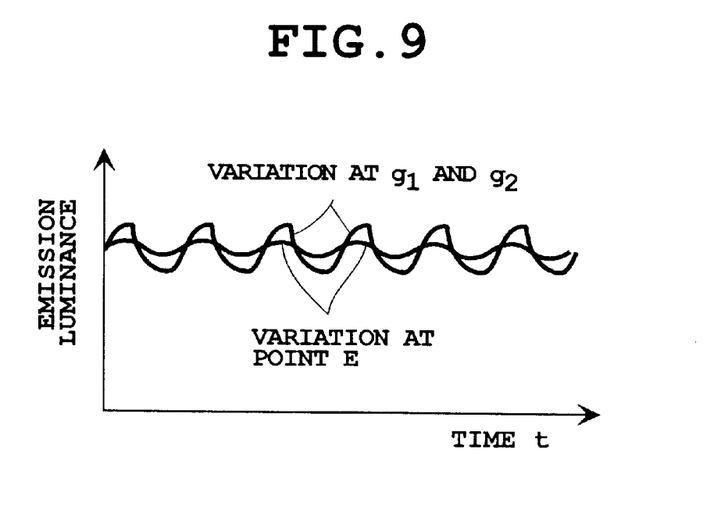
FIG. 9 is a graph showing a comparison of variations in luminance at bright spots of the electrodes of the AC lighting lamp with a variation in luminance at an intermediate position between the electrodes, according to the embodiments.

FIG. 8(A) shows an emission state of the electrodes. FIG. 8(B) shows a variation in luminance at the first bright spot $g_1$, FIG. 8(C) shows a variation in luminance at the intermediate point E, and FIG. 8(D) shows a variation in luminance at the second bright spot $g_2$. That is, when a lighting current is alternately applied to the first and second electrodes 25 and 26, emission with a significantly varying luminance is yielded at each of the first and second bright spots $g_1$ and $g_2$ as shown in FIGS. 8(B) and 8(D). However, stable emission with a reduced luminance difference is provided at a point between the electrodes, particularly the intermediate point E by means of to-and-fro discharge as shown in FIGS. 8(C) and 9.

In FIG. 5, a light output from the AC lighting lamp 22 is supplied to the tip portion of the scope via the light guide 20 and is then directed to a subject, which is then imaged by the CCD 12. The CCD driving circuit 13 reads out charges as image pickup signals, the charges being accumulated in the CCD 12 as pixels.

Figure 10A:
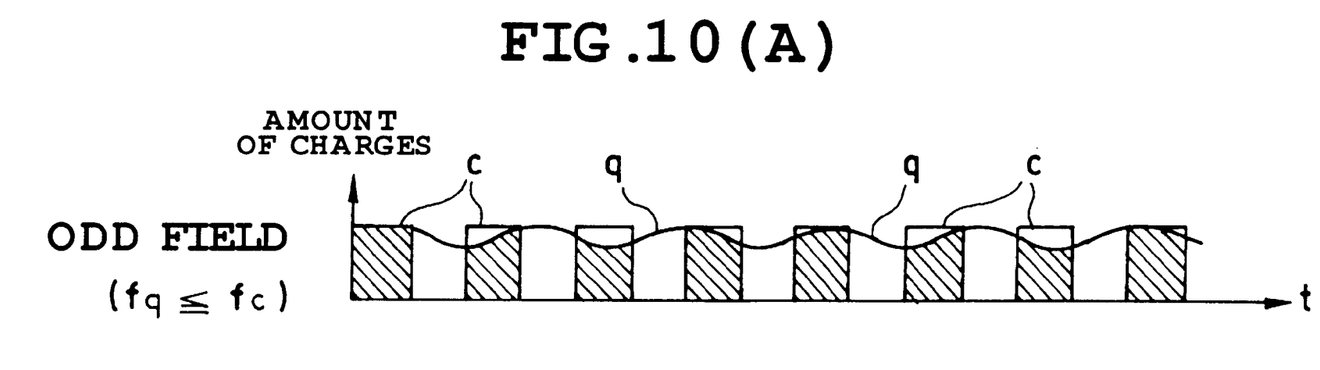
FIGS. 10(A) and 10(B) are timing charts showing a relationship between an amount of charges accumulated in a CCD and lighting of the lamp according to the embodiments.
Figure 10B:
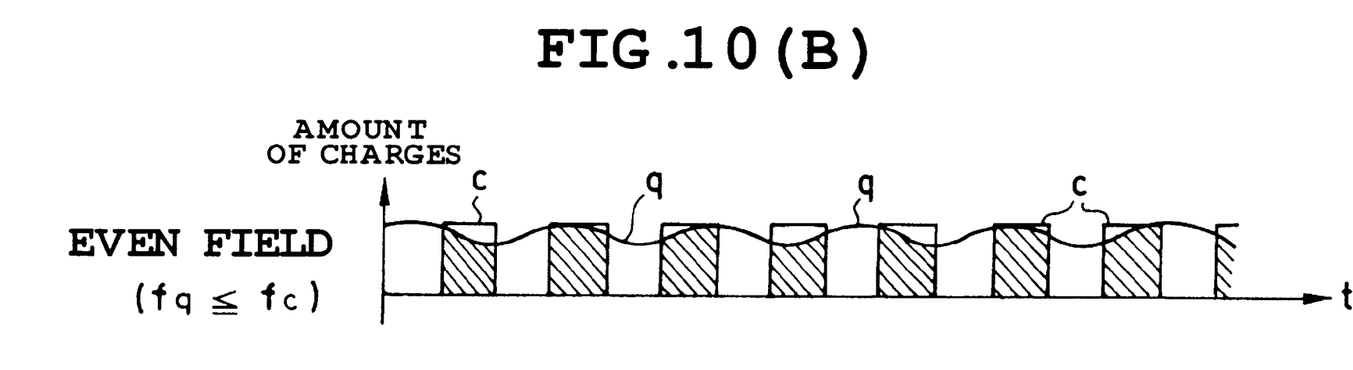

FIGS. 10(A) and 10(B) show a relationship between the accumulation of charges in the CCD 12 and the lighting of the lamp. If the lighting frequency $f_q$ of the lamp 22 is lower than the charge accumulation frequency (vertical synchronizing signal frequency) $f_c$ ($f_q \leq f_c$), then as shown by the odd and even fields in FIGS. 10(A) and 10(B), lightings q (emissions) are uniformly carried out within any time of charge accumulation c as shown by shaded portions. Hence, the amount of exposure does not significantly vary between the fields, thereby preventing possible flickers on the screen.

That is, an image pickup signal obtained from the CCD 12 is supplied to the signal processing circuit 16 via the amplifier 14 and the A/D converter 15. The signal processing circuit 16 subjects the signal to a predetermined process for forming a video, and outputs the processed signal to the monitor via the D/A converter 17. As a result, the video of the subject is displayed on the monitor, while preventing possible flickers on the monitor screen.

In the above embodiments, the entrance facet of the light guide 20 is arranged between the condensing points $G_1$ and $G_2$ or $G_3$ and $G_4$ of the bright spots $g_1$ and $g_2$, but it may be arranged at a position that is not close to any of the condensing points $G_1$ to $G_4$. This produces effects similar to those of the above embodiments.

As described above, according to the embodiments, in an electronic endoscope apparatus using an AC lighting light source, an entrance facet of a light guide is arranged at a position, for example, an intermediate position between two condensing points at which lights from bright spots at the tips of two electrodes of the AC lighting light source are condensed. Consequently, emission with a reduced variation in luminance is obtained, and if the lighting frequency is lower than the frequency of charge accumulation, an image can be picked up with a substantially uniform amount of emission. Therefore, an appropriate video is obtained without any flickers.

What is claimed is:

1. An electronic endoscope apparatus, comprising:

an AC lighting light source having condensing means;

a light guide that guides a light from the light source to a tip portion of a scope; and an image pickup element that picks up an image of a subject irradiated with a light via the light guide, wherein an entrance facet of said light guide is arranged between two condensing points and at a position that is not close to either of the condensing points so that lights from a bright spot at the tip of each of two electrodes of said AC lighting light source are condensed at the corresponding condensing point by said condensing means.

2. The electronic endoscope according to claim 1, wherein the condensing means comprises a reflector, wherein said reflector is arranged opposite said light guide relative to the light source, when an arc gap length between the two electrodes is defined as $\Delta 1$, then the entrance facet of said light guide is arranged close to a position located at a distance $+(\Delta 1/2)$ or $-(\Delta 1/2)$ from one of said condensing points formed on the basis of the shape of said reflector.

3. The electronic endoscope according to claim 1, wherein the condensing means comprises a reflector, wherein said reflector is arranged opposite the light guide relative to the light source and a condensing lens is arranged on the same side as that of the light guide relative to the light source, when the arc gap length between the two electrodes is defined as $\Delta 1$, the focal distance of said condensing lens is defined as f, and the distance from the front focal position of the condensing lens to the focal position of the reflector is defined as x, then the entrance facet of said light guide is arranged close to a position located at the distance $+\{f^2 \cdot \Delta 1/[2x(x+\Delta 1)]\}$ or $-\{f^2 \cdot \Delta 1/[2x(x+\Delta 1)]\}$ from one of said condensing points formed by the reflector and condensing lens.

* * * * *